United States Patent [19]

Ekholm

[11] 4,401,110

[45] Aug. 30, 1983

[54] PATIENT TREATMENT TABLE

[75] Inventor: Carl R. Ekholm, Elgin, Ill.

[73] Assignee: Standex International Corporation, Salem, N.H.

[21] Appl. No.: 177,427

[22] Filed: Aug. 12, 1980

[51] Int. Cl.³ .................................... A61F 5/00

[52] U.S. Cl. .................................... 128/70; 128/73

[58] Field of Search .................................... 128/70–74; 5/11, 62, 63; 269/323-327; 108/6, 7

[56] References Cited

U.S. PATENT DOCUMENTS

| | | | |
|---|---|---|---|
| 1,735,703 | 11/1929 | Williams | 128/73 |
| 3,113,770 | 12/1963 | Rutledge | 128/70 |
| 4,230,100 | 10/1980 | Moon | 128/70 |

*Primary Examiner*—Richard J. Apley
*Assistant Examiner*—David J. Brown
*Attorney, Agent, or Firm*—Mason, Kolehmainen, Rathburn & Wyss

[57] ABSTRACT

A patient treatment table is provided wherein a patient table which is pivotally mounted on an upper frame may be tilted from a position near the vertical to a horizontal position in engagement with the upper frame and the upper frame and patient table are elevated to a desired adjustable height relative to a fixed lower base member in one smooth continuous motion. Conversely, when a patient is to be removed from the table the upper frame and table are lowered to a minimum height position and the table is tilted to a near vertical position again in one smooth continuous movement.

24 Claims, 16 Drawing Figures

Fig. 11
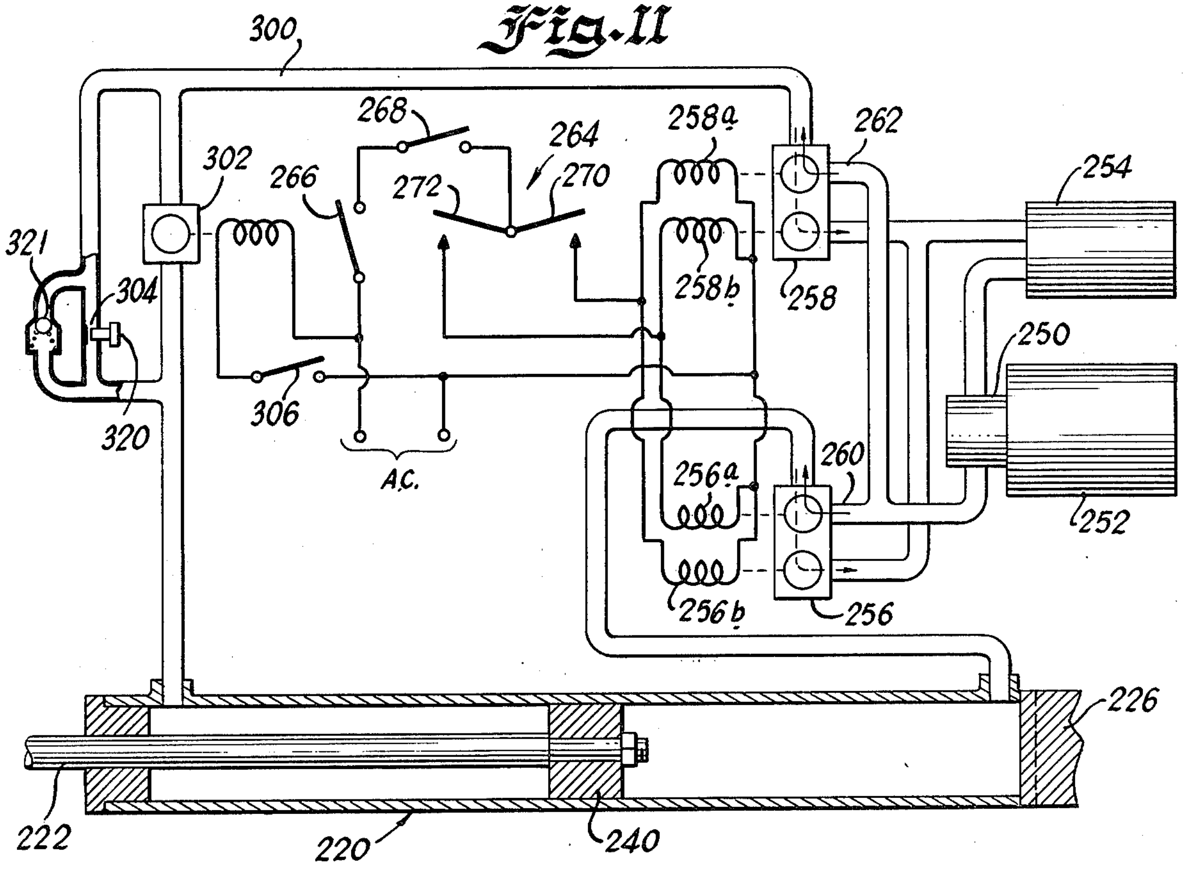
Fig. 16
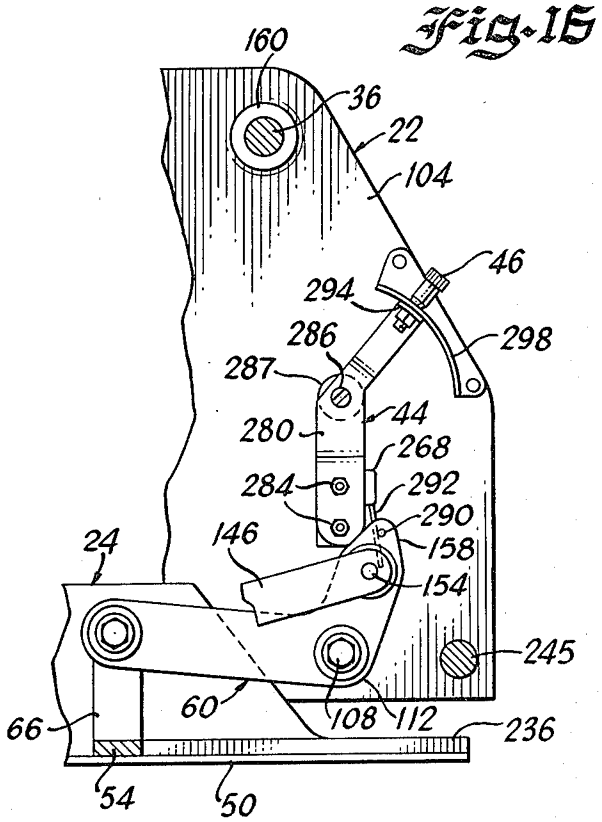
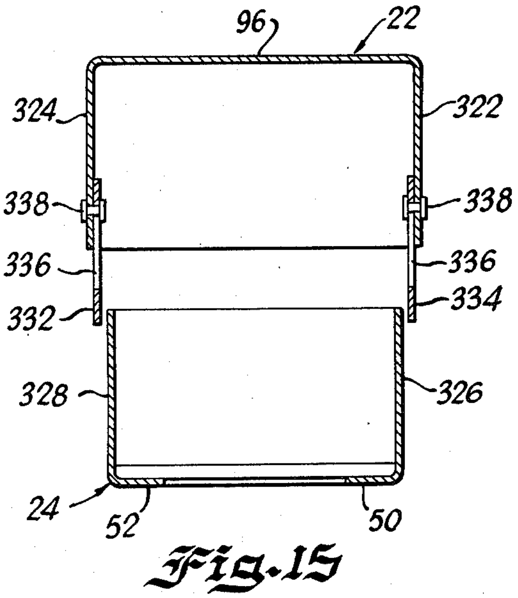
Fig. 15

PATIENT TREATMENT TABLE

This invention relates generally to patient treatment tables and more particularly to an improved patient treatment table which is particularly suited for chiropractic adjustment and in which both the raising and lowering the and tilting movements of the patient treatment table can be effected in an economical, efficient and stable manner.

BACKGROUND OF THE INVENTION

Historically, chiropractic adjusting tables would be used by the chiropractor for his professional lifetime. The tables were made to suit short practitioners and extensions could be rather permanently attached to raise the table in two-inch increments from a twenty inch minimum to a twenty-six inch maximum which generally suited various builds and heights of doctors.

In later years, as practices have grown, a doctor may add additional units and then bring in an associate. If the doctors were not the same height, or did not use the same adjusting technique, a fixed height became a detriment and this problem became amplified in the larger clinics where many doctors were practicing.

In order to alleviate this situation, various arrangements have been proposed to provide chiropractic adjustment tables wherein the height can be varied. Generally, these tables include an elongated table frame upon which are positioned cushioned sections which may slide along the frame to accommodate different-sized persons. They also generally include a foot rest at one end of the frame. The frame itself is arranged to be adjusted in height by an appropriate hydraulic system to raise the entire frame in a vertical direction. In addition, the tables are generally capable of being tilted towards an upright position and the foot rest is utilized as a support for the patient's feet when the table is moved toward the vertical position.

Many of these adjustable height tables are very slow acting or have a very complex means for changing from the inclined or tilting movement to the purely vertical movement of the frame. Some arrangements use a mechanical selector interlock that changes the direction mode but only at a certain cycle termination point so that the mechanism can be engaged or disengaged.

Many of these prior art arrangements have used two hydraulic cylinders for the multi-directional movement. However, these arrangements also require electrical or mechanical trips or interlocks to eliminate any chance of the table traversing two directions at the same time which would expose the patient to the possible danger of the footstep not being in the same position when the patient gets off the table as it was when the patient stepped on it. Such a condition can be particularly disturbing to many patients who have circulatory problems, lack of coordination, impaired vision or other possible maladies.

Some of the adjustable height prior art table arrangements have employed a single hydraulic cylinder to accomplish both tilting of the patient table for loading and unloading the patient and elevation of the table when in a horizontal position to a suitable hight for the chiropractor. However, these arrangements employ various mechanical cam or ramp actuated latches which come into action or release throughout the hydraulic cylinder motion. These arrangements appear difficult to adjust originally and virtually impossible to service in the field should a malfunction occur. Also, the motor and pump units and hydraulic cylinders on such single cylinder arrangements are virtually buried in the equipment thus severely limiting even simple repairs or adjustments.

In all of these adjustable height chiropractic table arrangements, the problem has been to provide a mechanism by means of which the adjusting table can be raised in height in order to suit the needs of the particular doctor while at the same time providing a solid, stable support for the table in its elevated position which will promote a secure feeling for the patient and will permit the doctor to make appropriate adjustments to the patient without having to compensate for side sway or a soft rubbery feel of the patient table when supported in its elevated position. Certain adjustable height arrangements have supported the table in its elevated position by means of a single center post. However, such arrangements do not provide a stable support for the elevated table when adjustments to the neck or other extremities are made by the doctor.

While another prior art arrangement has supported the elevated table at the four corners thereof, the linkage employed to elevate the table to an adjustable height is supported on rollers which provide an insecure, rubbery supporting structure which does not promote a secure feeling on the part of the patient or permit the doctor to be sensitive to the patient's condition. Furthermore, the linkage arrangements of such a structure are subject to side sway, particularly when the joints of the linkage begin to wear. Furthermore, in such prior art arrangement, the linkages used to raise and lower the table are all exposed so that many potentially harmful pinch points are accessible to both the doctor and the patient with the attendant possibility of personal injury thereto.

BRIEF DESCRIPTION OF THE PRESENT INVENTION

The arrangement of the present invention provides an adjustable height patient treatment table wherein a solid secure support for the table when in an elevated position is provided by means of a single hydraulic control cylinder and simplified linkage arrangement, the linkage arrangement being enclosed within the housing of the upper adjustable height frame so as to minimize personal injury to both the patient and the doctor. Furthermore, the two motions of tilting the patient table from a position near the vertical to a horizontal position and then raising the table to a desired adjustment height are accomplished in a smooth and continuous manner without the use of any mechanical interlocks or adjustments on the part of the doctor.

With applicant's arrangement the delay required to actuate mechanical interlocks or other controls when changing from the tilting motion of the table to elevation thereof are totally eliminated so that both movements are sequentially accomplished in one smooth continuous motion. This motion is provided by employing a single hydraulic cylinder the piston rod of which is connected directly to an offset arm portion on the patient table to tilt the same to a near vertical position and the hydraulic cylinder itself is floatingly attached to a linkage which interconnects the upper frame and a base or supporting frame so that the application of fluid under pressure to the hydraulic cylinder is able to accomplish both the tilting and elevating motions in one continuous movement, and without requiring the adjustment of any mechanical interlocks or controls on the part of the doctor.

A similar motion is provided when the patient is to be removed from the table, the table being automatically lowered to a minimum height position in which the table is tilted to a near vertical position with the foot rest position close to the floor. Since the patient table is raised and lowered many times each day, the saving in doctors' time by eliminating any delay in shifting from a tilting motion to an elevating motion, is substantial.

An additional feature of applicant's invention is that it is impossible to tilt the table to a vertical position before the table has been lowered to the minimum height position in which the foot rest is correctly positioned relative to the floor. This effect is achieved by supplying fluid under pressure to the piston rod side of the cylinder while exhausting the head end side of the cylinder. Until the floating cylinder has moved back to its initial position with the table at its minimum height it is impossible for the cylinder to tilt the table.

In accordance with a further feature of the invention, a solenoid valve and restrictive port arrangement is provided for exhausting the cylinder when the table is being tilted back to a horizontal position so that the cylinder is exhausted slowly and a cushioning effect is produced for the last few degrees of travel to the horizontal position. The solenoid valve is activated in response to movement of the table near the horizontal and closes so that the cylinder can only be exhausted through the restricted port. Furthermore, the point at which the cushioning effect is initiated may be varied by adjusting the table position at which the valve is actuated.

BRIEF DESCRIPTION OF THE DRAWINGS

The invention, both as to its organization and method of operation, together with further objects and advantages thereof, will best be understood by reference to the following specification taken in connection with the accompanying drawings, in which:

FIG. 8 is a view similar to FIG. 7 but showing the upper housing in its lowered position;

FIG. 11 is a diagram showing the electro-hydraulic control system of the present invention.

FIG. 15 is a fragmentary view similar to FIG. 5 but of an alternative embodiment of the invention; and FIG. 16 is a view similar to FIG. 3 but showing the height adjusting lever in a different position.

DETAILED DESCRIPTION OF THE PREFERRED EMBODIMENT

Figure 1:
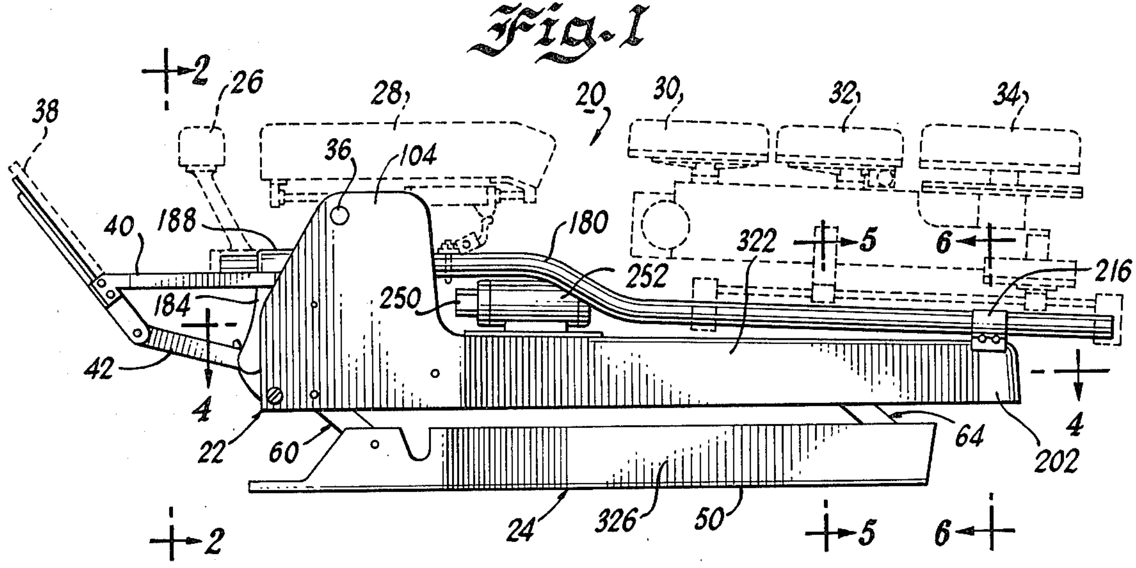
FIG. 1 is a side elevational view of the patient treatment table of the present invention showing the patient table in a horizontal and elevated position.

Referring now to the drawings, the patient treatment table of the present invention is therein illustrated as comprising a patient table indicated generally at 20, an upper supporting frame or base indicated generally at 22, and a lower supporting frame or base indicated generally at 24. As indicated by dotted lines in FIG. 1, a number of cushion supporting structures 26, 28, 30, 32 and 34 may be mounted on the patient table 20 and may be adjusted so as to support various portions of the patient's body when lying prone on the table 20 so that chiropractic adjustments can be made on the patient. However, it will be understood that various other types of cushions or other patient supporting structures may be employed on the patient table 20 insofar as the present invention is concerned.

Figure 9:
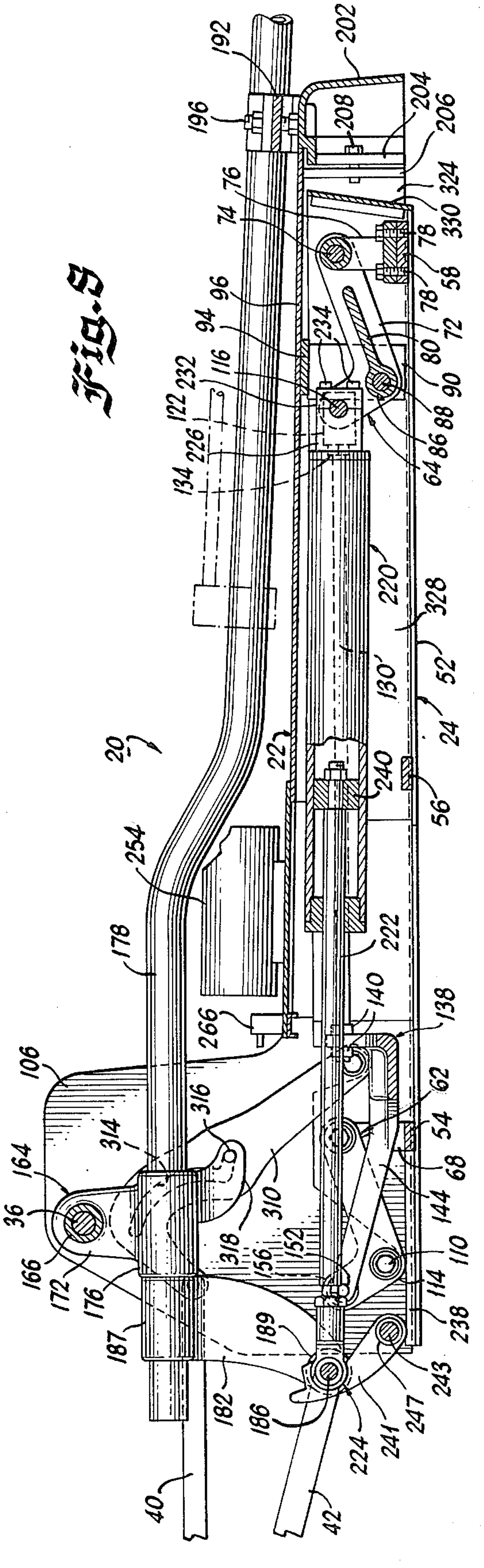
FIG. 9 is a view similar to FIG. 8 but with the patient table shown tilted upwardly to a position near the vertical.

The patient table 20 is pivotally connected to the foot of the upper base 22 for movement about the transverse shaft 36 thereof so that the patient table 20 can be moved from the horizontal position shown in FIG. 8 to a position near the vertical as shown in FIG. 9. As in conventional chiropractic adjustment tables, a footstep platform 38 which is pivotally interconnected with the upper supporting frame 22 by means of the footstep draw bars 40 and the footstep alignment bars 42, is arranged to be positioned horizontally at a position near the floor when the patient table 20 has been tilted upwardly to a position near the vertical, as shown in FIG. 9. The patient is then able to board the table by stepping onto the platform 38 and leaning against the cushions 26–34. As the table 20 is then tilted back to a horizontal position the platform 38 is moved away from the feet of the patient so that they freely rest upon the cushion 26.

In accordance with an important aspect of the present invention, the patient table 20 is arranged to be tilted from the near vertical position shown in FIG. 9 to the horizontal position shown in FIG. 8 and thereafter the upper supporting frame 22 and table 20 elevated to a desired height relating to the base 24 in one smooth continuous motion. Conversely, when the table 20 is positioned in an elevated position such as shown in FIG. 1 and the patient is to be removed from the table, the table 20 and upper supporting frame 22 are lowered as a unit to the minimum height position shown in FIG. 8 and the table 20 is then tilted to the near vertical position shown in FIG. 9 in one smooth continuous motion. Both of the above-described motions are achieved without the use of any mechanical interlocks or separate controls which must be manipulated by the doctor in shifting from a tilting movement of the table 20 to an elevational movement of the upper supporting frame 22 in table 20. Furthermore, the height to which the table 20 is raised may be adjusted within a range from the minimum height position shown in FIG. 8 to the maximum height position shown in FIGS. 1 and 7. When the table 20 is in the position shown in FIG. 8, the surface of the cushions 26–34 is approximately 22 inches from the floor and when the table 20 is in the position shown in FIG. 1, the level of these cushions is approximately 28 inches from the floor. A desired position anywhere within this range may be selected by the doctor by adjustment of a height adjustment lever 44, as will be described in more detail hereinafter. Also, the lever 44 may be locked in adjusted position by means of a thumbscrew or the locking nut 46 so that each time a new patient is loaded onto the table the table is moved to the same adjusted height for the doctor. However, if another doctor uses the table and desires a different adjustment height for the patient, he can adjust the lever 44 to a different position and the table 20 will be brought to this new position automatically.

Figure 2:
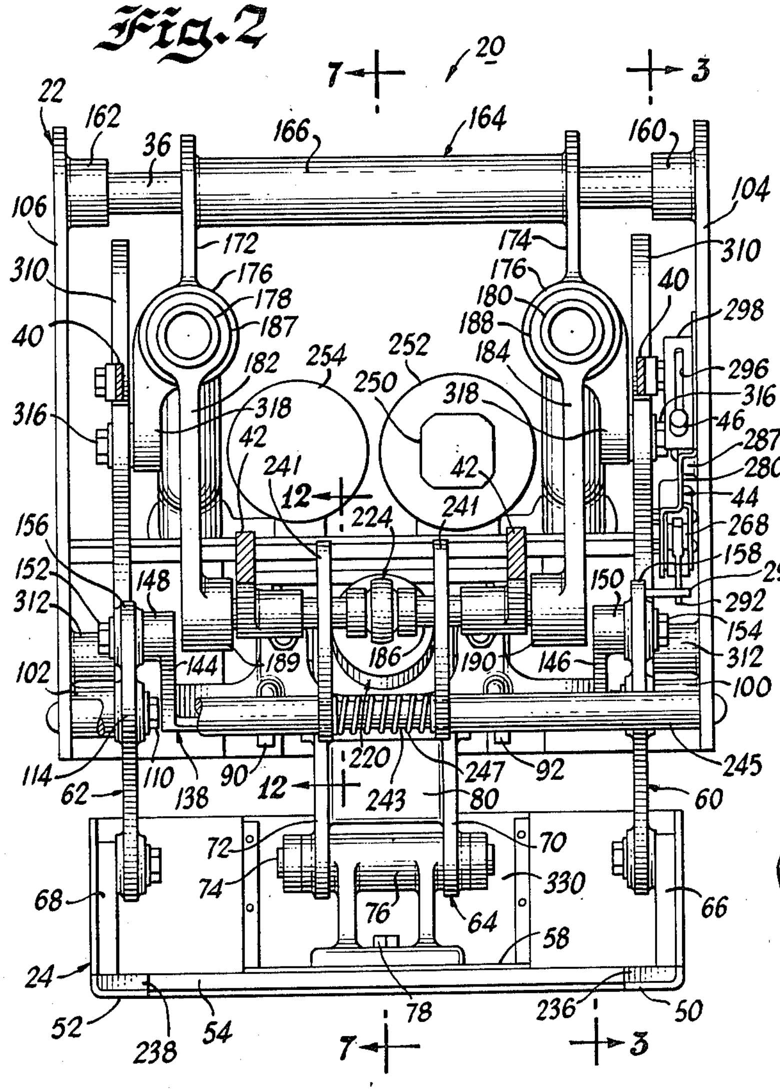
FIG. 2 is a sectional view taken along the lines 2—2 of FIG. 1.
Figures 4, 5, 6, 14:
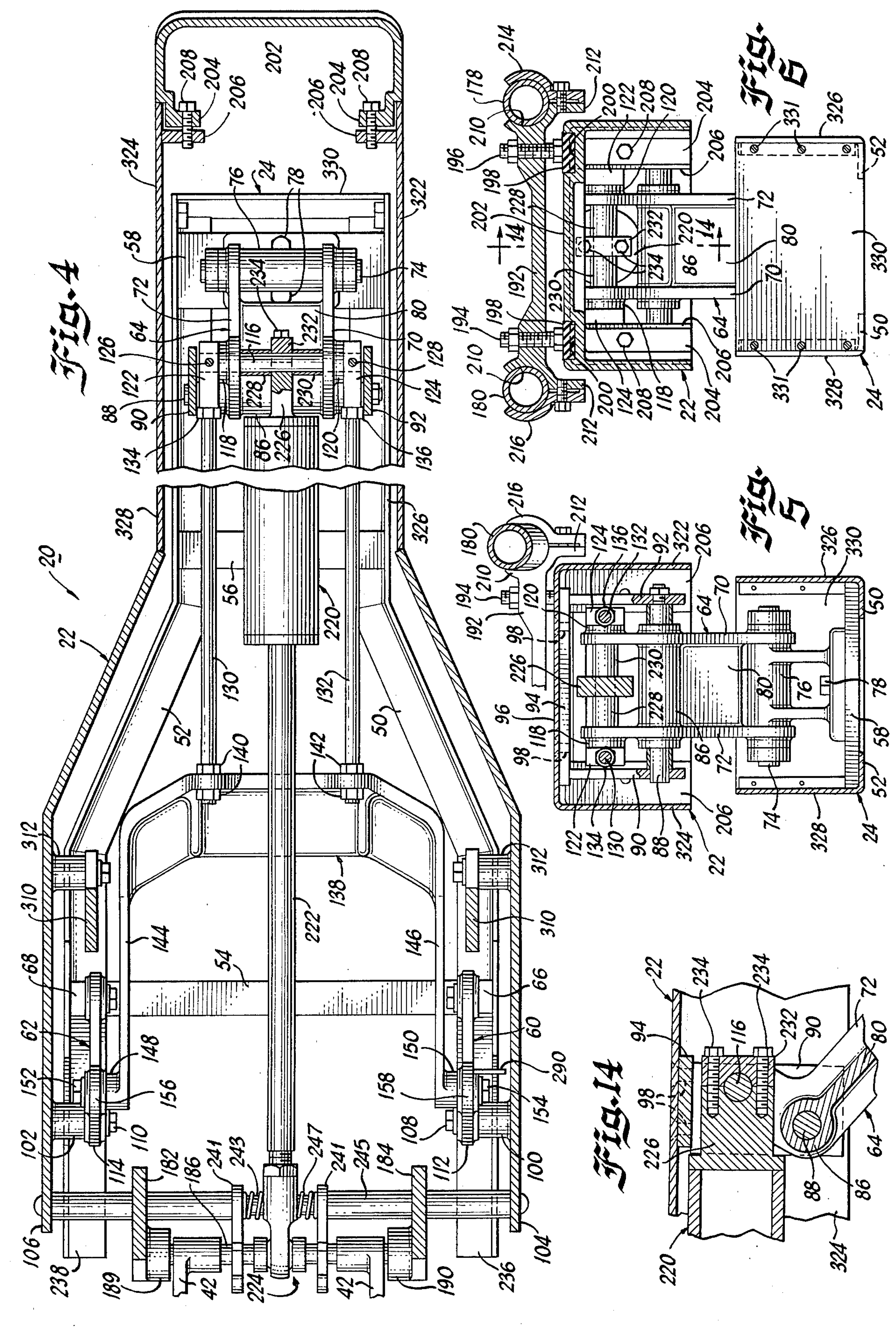
FIG. 4 is a sectional view taken along the line 4—4 of FIG. 1.
FIG. 5 is a sectional view taken along the lines 5—5 of FIG. 1.
FIG. 6 is a sectional view taken along the lines 6—6 of FIG. 1.
FIG. 14 is a sectional view taken along the lines 14—14 of FIG. 6.

Considering now the manner in which the upper supporting frame 22 is pivotally mounted on the lower base member 24, the base member 24 comprises the side rails 50 and 52 which are interconnected with the transverse rails 54, 56 and 58 to provide a sturdy supporting base for the patient treatment table of the present invention. The upper supporting frame 22 is pivotally mounted on the base 24 by means of a pair of rear bell cranks or rocker arms 60, 62 and a front rocker arm assembly indicated generally as 64. The longer arms of the rocker arms 60, 62 are pivotally mounted in the pillow blocks 66, 68 which are supported on the cross rail 54, as best illustrated in FIG. 2. The front rocker arm assembly includes the pair of downwardly extending arm portions 70, 72 which are pivotally mounted on the shaft 74 supported in the front pillow block 76 which is mounted on the front cross rail 58 by means of the bolts 78. The arms 70, 72 are interconnected by means of an integrally formed rib 80 so that an extremely solid, stable support is provided for the front or head end portion of the upper supporting frame 22. With such an arrangement a substantial portion of the lower base 24 and the upper supporting frame 22 may be relatively narrow, as best illustrated in FIG. 4, to permit the doctor to work directly over the patient while providing a structure wherein the upper frame 22 and table 20 may be held in an elevated position without producing undesirable side sway of the supported table.

The front rocker arm assembly 64 is provided with an intermediate sleeve portion 86 which is rotatably mounted on the shaft 88 journalled in the depending arms 90, 92 of a pillow block 94. The pillow block 94 is secured to the top wall 96 of the upper supporting frame 22 by means of the flat headed screws 98. In a similar manner an intermediate point on the rear rocker arms 60, 62 is rotatably mounted on the upper supporting frame 22. More particularly the bosses 100, 102 which are secured to the side panels 104, 106, respectively of the upper supporting frame 22 are threaded to receive the bolts 108, 110 the shoulders of which form a bearing for the bosses 112, 114 formed in the intermediate portion of the rocker arms 60, 62.

In order to interconnect the rocker arm 60, 62 with the front rocker arm assembly 64 so that they may be pivoted in unison, a shaft 116 is rotatably mounted in the bosses 118, 120 formed in the ends of the short arm portions of the assembly 64 and the threaded blocks 122, 124 are secured to the shaft 116 by means of the set screws 126, 128, respectively. A pair of threaded rods 130, 132 are secured in adjusted position on the blocks 122, 124 by means of the nuts 134, 136, the rods 130, 132 being adjustably connected to a cross head 138 by means of the nuts 140 and 142. The cross head 20 is provided with a pair of rearwardly extending arms 144, 146 which are pivotally connected to the short arm portions of the rocker arm 60, 62. More particularly, the arms 144, 146 are provided with the boss portions 148, 150 into which the bolts 152, 154 are threaded, the shoulders of these bolts being journalled in the ends of the short arm portions 156, 158 of the rocker arms 62, 60 as best illustrated in FIG. 4.

Considering now the structure of the patient table 20 and the manner in which this table is pivotally mounted on the upper supporting frame 22, the shaft 36 is journalled in the rearwardly extending bushings 160, 162 formed in the side walls 104, 106 of the supporting frame 22. A carriage indicated generally at 164 is pivotally mounted on the shaft 36 and includes a sleeve portion 166 which is rotatably positioned on the shaft 36 and is provided with a pair of depending flange portions 172, 174 having integrally formed therewith the sleeve portions 176 which are secured to the tubular side rails 178, 180 of the patient table 20. A pair of offset arms 182, 184 are provided with sleeve portions 187, 188 which are also secured to the side rails 178, 180 and a shaft 186 is journalled in the bosses 189, 190 formed in the ends of the offset arms 182, 184. The front or head ends of the side rails 178, 180 are connected to a rest bar 192 (FIG. 6) within which are mounted the bolts 194, 196 with the downwardly extending heads of the bolts 194, 196 being adapted to seat on a pair of resilient cushions 198 provided in the recesses 200 formed in the upper surface of a nosepiece portion 202 of the upper frame 22. The removable nosepiece 202 is provided with rear flanges 204 which is secured to the vertical side rails 206 of the upper frame 22 by means of the bolts 208. The rest bar 192 is provided with arcuate portions 210 which are shaped to receive the side rails 178, 180 and the depending flange portions 212 to which are bolted arcuate clamping members 214, 216 so that the side rails 178, 180 of the table 20 are removably secured to the rest bar 192.

As discussed generally heretofore, a single hydraulic control cylinder indicated generally at 220 is provided to achieve both the tilting movement of the patient table 20 and the elevation of the upper support member 22 and table 20 as a unit relative to the lower base 24. To this end, the piston rod 222 of the cylinder 220 is connected to the shaft 186 by means of the ball joint connection 224 and the head end of the cylinder 220 is provided with a forwardly extending vertical flange portion 226 (see FIG. 4) which is pivotally connected to the shaft 116 which interconnects the short arm portions of the rocker arm assembly 64. More particularly, the flange 226 is positioned between the sleeves 228 and 230 on the shaft 116 and the end portion of the flange 226 is formed as one half of a split bearing which is positioned in engagement with the shaft 116, the other half of the split bearing 232 being secured to the flange 226 by means of the bolts 234. When it is desired to remove the cylinder 220 for service and repair, the nosepiece 202 is removed with the upper frame 22 when the frame 22 is supported on blocks in an elevated position. Also the front wall 330 of the base 24 may be removed by unscrewing the screws 331 (FIG. 6) to provide easy access to the bolts 234 which hold the split bearing 232 in place. Once the bearing 232 is removed the cylinder 220 can then be removed from the rear of the unit after the piston rod 222 is disconnected.

Figure 7:
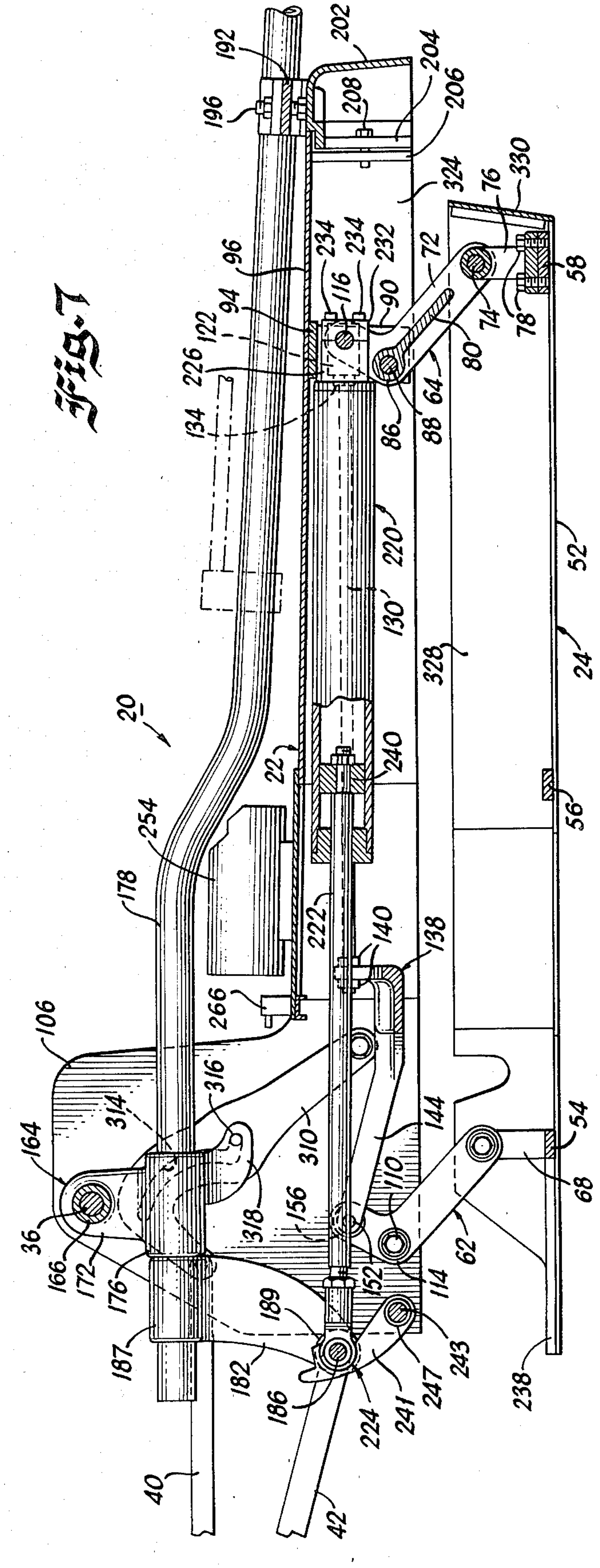
FIG. 7 is a sectional view taken along the lines 7—7 of FIG. 2.

Considering now the operation of the single cylinder 220 to control both the tilting and the elevation motions in one continuous movement, when the patient table is tilted near the vertical, i.e., the position shown in FIG. 9, the upper supporting frame 22 is positioned in its minimum height position with the rear rocker arms 60,

62 resting on the support rails 236, 238 provided in the lower base 24. Also, when the patient table 20 is in the tilted position shown in FIG. 9, the piston 240 is positioned near the head end of the cylinder 220. If oil under pressure is now introduced into the head end of the cylinder on the right of the piston 240 the piston rod 222 moves to the left, as viewed in FIG. 9 and tilts the patient table back to a horizontal position by rotation of the carriage 164 about the shaft 36. Lowering of the patient table 20 continues until the horizontal position is reached and the bolts 194, 196 engage the cushions 198 provided in the nosepiece 202 at which time the piston rod 222 is prevented from further movement to the left. However, since the head end of the cylinder 220 is floatingly connected to the short arm portions of the front rocker arm assembly 64 through the shaft 116 the continued application of fluid under pressure to the head end of the cylinder now causes the cylinder itself to move to the right and exert a force on the upper end of the rocker arm assembly 64 so as to rotate this assembly about the shaft 74 which is supported in the pillow block 76 mounted in the base member 24. At the same time this force is transmitted through the rods 130, 132 and the cross head 138 to the rear rocker arm 60, 62 so that these rocker arms are also rotated in unison about the rear pillow blocks 66, 68. As a result, the upper supporting frame 22 with the patient table carried thereon in a horizontal position, is elevated from the position shown in FIG. 8 to an upper position relative to the base member 24 as shown in FIG. 7.

It will be noted that since fluid under pressure is continuously supplied to the head end of the cylinder during this operation the tilting and elevational movements are accomplished in one continuous motion without the adjustment of any mechanical interlocks or the adjustment of controls on the part of the doctor. In the same manner, when it is desired to remove the patient from the table, fluid under pressure is supplied to the piston rod side of the piston 240 while at the same time the head end of the cylinder is exhausted to the oil rservoir. When this occurs the piston rod 222 cannot immediately move to the right because the cylinder 220 is floatingly connected to the rocker arm assembly 64. Accordingly, as the head end of the cylinder 220 is exhausted the cylinder 220 moves to the left from the position shown in FIG. 7 to the position shown in FIG. 8 so that the upper supporting frame 22 and patient table 20 are lowered to the minimum height position shown in FIG. 8. However, when the cylinder 220 has been moved to the left to the position shown in FIG. 8 the rocker arm 60, 62 are in engagement with the base pads 238 so that the cylinder 220 is prevented from further movement to the left. Accordingly, the continued application of oil under pressure to the piston rod side of the piston 240 now results in movement of the piston to the right and the consequent tilting of patient table 20 to a position near the vertical, as shown in FIG. 9. Here again, the movements of lowering the patient table to the minimum height position shown in FIG. 8 and then tilting the table upwardly to remove the patient are accomplished in one continuous motion without requiring the actuation of any mechanical interlocks, or the like. It should also be pointed out that until the table 20 is moved to the minimum height position shown in FIG. 8 and the cylinder 220 has become fixed in position by engagement of the rocker arms 60, 62 with the pads 236, 238, it is impossible to tilt the table 20 by application of fluid pressure to the rod side of the piston 240. However, as soon as the cylinder 220 becomes fixed this application of fluid pressure automatically causes the table 20 to tilt upwardly to the patient unloading position.

Figures 9, 10, 12, 13:
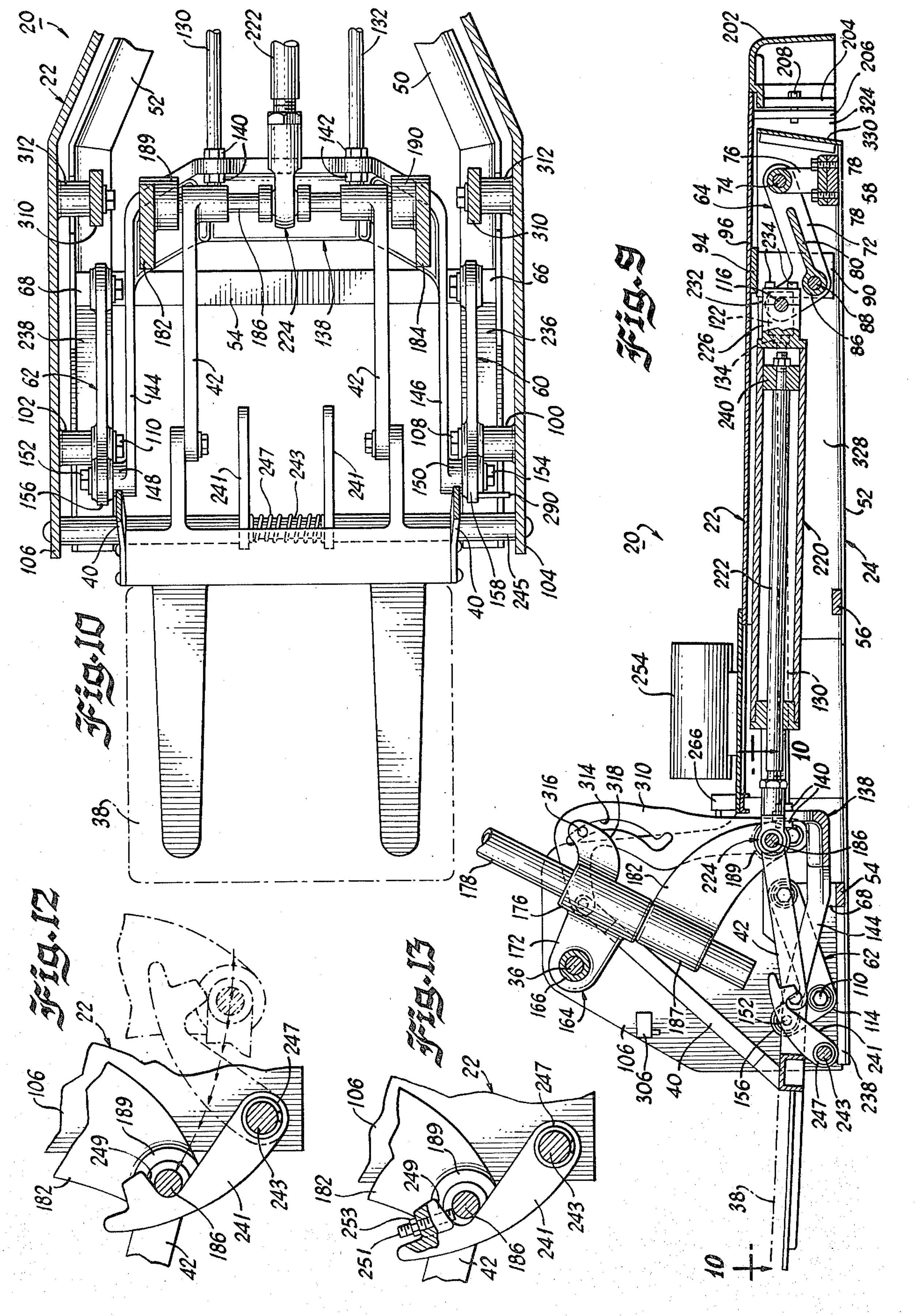
FIG. 10 is a sectional view taken along the lines 10—10 of FIG. 9.
FIG. 12 is an enlarged view of the link limiter used in the table of FIG. 1.
FIG. 13 is a view similar to FIG. 12 but of a modified link limiter.

While it has been indicated that movement of the piston 240 to the left is limited by engagement of the table bolts 194, 196 with the nosepiece 202, since pressure continues to be applied to the head end of the cylinder and this pressure is substantial because it is used to elevate the upper frame 22 and table 20 with perhaps a three hundred pound patient thereon, there is a possibility that the tubular side rails 178, 180 of the table 20 may become bent or deformed with continued usage of the table. In accordance with a further important aspect of the present invention, deformation of the side rails 178, 180 is avoided by providing a positive stop for the piston rod 222 which prevents movement of the piston 240 to the left when the table 20 engages the nosepiece 202. More particularly, a pair of link limiters 241 are rotatably mounted on the reduced diameter portion 243 of a transverse shaft 245 which extends between the side walls 104, 106 of the upper frame 22. A spring 247 is positioned between the link limiters 241 to urge them against the shoulders formed in the shaft 245. Hook portions 249 are formed in the outer ends of the link limiters 241 which are adapted to engage the shaft 186 as the table 20 is lowered and the piston rod 222 moves the shaft 186 rearwardly. When the shaft 186 is moved into the hook portions 249 it is thereafter positively prevented from moving further to the left as viewed in FIG. 8 since the shaft 186 is itself pivotally mounted for rotation about the shaft 36 and would tend to move along the arc shown in dotted lines in FIG. 12 so that a positive stop is provided for the piston rod 222.

When the table 20 engages the nosepiece 202 the shaft 186 may not always be positioned at exactly the same location with different units due to manufacturing tolerances and the like. To accommodate said tolerances the arrangement shown in FIG. 13 may be employed wherein a set screw 251 is threaded into the hook portion 249 of each link limiter 241 and may be locked in adjusted position by the nut 253. The set screw 251 may thus be adjusted to provide a positive stop for the piston rod 222 at the exact point where the table 20 engages the nosepiece 202, thereby avoiding continuous strain on the side rails 178, 180.

It will be noted that the frame 22 and 20 are elevated by exerting a force on the relatively short arm portions of the rocker arm assembly 64 and the rocker arms 60, 62 to pivot these elements about their pivotal mountings in the frame 22. Such an arrangement is mechanically inefficient because force is applied to the short arm portion with the load, i.e., the frame 22 and table 20, is positioned between force applied and the pivot point on the base 24. In fact, such an arrangement is mechanical inefficient by a ratio of three to one, approximately. However, once the table 20 has been raised to the elevated position shown in FIG. 7, the additional load placed on the table as the doctor adjusts the patient is relatively ineffective to cause movement of the table so that a solid secure support is provided for the table 20 with the rocker arm arrangement of the present invention.

It will be noted that the patient table 20 is held in the elevated position shown in FIG. 7 solely by the containment of fluid within the cylinder 220. It is therefore important that the valving arrangement employed to control the cylinder 220 be absolutely leak-proof since otherwise the patient table 20 would not remain in its desired adjusted position. To this end, the electromechanical arrangement shown in FIG. 11 is employed wherein the pump 250 which is driven by the motor 252 supplies oil under pressure from the tank 254 to a pair of three-way solenoid valves 256 and 258 through the inlets 260 and 262, respectively. Preferably the valves 256 and 258 are of the high pressure impact type and are three-way normally closed valves which may be operated at pressures of 800 p.s.i. or greater without permitting any leakage from either side of the cylinder 220. A preferred valve is the Series 20, Model H23 valve manufactured by Peter Paul Electronics of New Britain, Conn. Such valves employ dual solenoids for three-way valve action and when neither solenoid is energized all ports are closed. Thus, the valve 258 is provided with the solenoids 258*a* and 258*b* and the valve 256 is provided with the solenoids 256*a* and 256*b*.

In order to control the solenoid valves 256 and 258 a foot switch 264 is provided to supply current to these valves. More particularly, the AC line is connected through the normally closed control switches 266 and 268, to be described in more detail hereinafter, to the foot switch 264. When the arm 270 of the switch 264 is depressed AC current is supplied to the solenoid winding 258*a* of the solenoid valve 258 and to the solenoid 256*b* of the valve 256. When these solenoids are energized oil under pressure is supplied through the valve 258 to the rod end of the cylinder 220, as indicated by the full line arrow in FIG. 11, while at the same time the valve 256 is connected to exhaust the head end of the cylinder to the oil tank 254, as indicated by the dotted arrow in FIG. 11. When the foot switch arm 272 is depressed AC current is supplied to the solenoids 258*b* and 256*a* so that oil under pressure is supplied to the head end of the cylinder from the valve 256, as indicated by the full line arrow in FIG. 11 and at the same time the rod end of the cylinder 220 is exhausted to the oil tank through the valve 258, as indicated by the dotted arrow in FIG. 11. When neither arm of the foot switch 264 is depressed no current is supplied to the solenoids of the valves 256 and 258 and all of their ports are closed so that no oil can escape from either side of the cylinder 220. Accordingly, once the patient table 20 has been moved to an elevated position, as shown in FIG. 7 and the foot switch 264 is released, the patient table 20 will remain at that height until the foot switch 264 is again depressed. Such operation is achieved because of the exceedingly high pressure rating of the valves 256, 258 and the fact that they provide bubble-tight sealing at the pressure at which cylinder 220 is operated. Preferably the pump 250 is operated so that the pressure of 800 p.s.i. is available for the actuation of the cylinder 220. However, the valves 256, 258 described above have the ability to withstand substantially greater pressures so that the doctor is assured that the patient table 20 will remain at its adjusted height.

Figure 3:
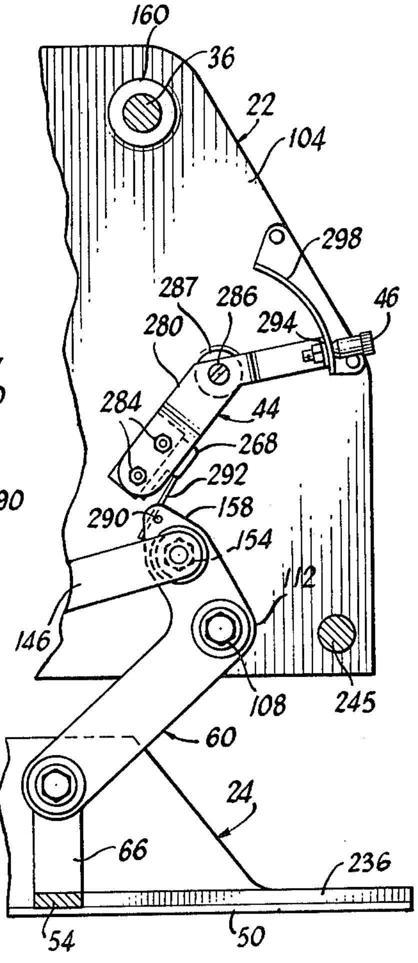
FIG. 3 is a sectional view taken along the lines 3—3 of FIG. 2.

As discussed generally heretofore the height adjustment lever 44 is provided so that the doctor can control the height to which the patient table 20 is elevated so as to suit his particular requirements. More particularly, the control lever 44 is provided with an arm portion 280 (FIG. 3) on which the switch 268 is mounted by means of the bolts 284, the lever 44 being pivotally mounted on the boss 287 formed in the side panel 106 by means of the screw 286. A pin 290 (FIG. 2) which is mounted in the upper end of the short arm portion of the rocker arm 60, extends transversely to the rocker arm 60 and is adapted to engage the arm 292 of the switch 268 so that this switch is opened when the upper supporting frame 22 and patient table 20 have been elevated to the desired height. The other end of the lever 44 is provided with an end flange 294 in which the thumb screw 46 is mounted, the screw 46 extending through the slot 296 in a bracket 298 which is mounted on the side wall 104. Accordingly, if the doctor wishes to change the height setting he merely loosens the thumb nut 46 and rotates the lever 44 to the desired position. Preferably the bracket 298 may have suitable indicia corresponding to the adjusted height of the table 20. As the upper frame 22 is elevated the rocker arm 60 rotates about the pivot 108 and when it has been elevated to the desired point the pin 290 opens the switch 268. When the switch 268 is opened the solenoid valves 256 and 258 are deenergized irrespective of the fact that the doctor is still depressing the foot switch 264. Accordingly the patient table 20 is automatically stopped at the desired height determined by the setting of the lever 44 and not by the point at which the doctor releases the foot switch 264. If, for example, a particular doctor desires that the patient table be elevated a relatively small amount, the lever 44 may be moved to the position shown in FIG. 16 wherein it will be observed that the switch 268 is opened when the patient table 20 has been elevated by only a small amount.

In accordance with a further aspect of the invention, an arrangement is provided for restricting the flow of fluid from the cylinder 220 when the patient table 20 is being lowered and reaches a position a few degrees from the horizontal. Accordingly, a cushioning effect is provided for the last few degrees of travel of the table 20 to the horizontal so that it will come gently into contact with the nosepiece 202. Furthermore, the point at which this cushioning action takes effect may be adjusted so that the doctor can vary the amount of cushioning to suit himself. However, the cushioning is removed when it is desired to tilt the table upwardly to unload the patient so as to avoid the delay which would result if the restriction were maintained during unloading. More particularly, the pressure line 300 from the solenoid valve 258 is supplied to the rod side of the cylinder 220 through a two-way solenoid valve 302 and a one-way acting restriction port 304 which is connected in parallel with the solenoid valve 302 to the rod side of the cylinder 220.

The solenoid valve 302 is controlled by the switch 306 which is arranged to be closed, so that the valve 302 is open, at all times except when the patient table 20 is within a few degrees of the horizontal. Preferably, the switch 306 is controlled by movement of one of the footstep draw bars 40 because these members are being moved relatively rapidly as the table 20 nears the horizontal position. More particularly, footstep draw bars 40 are pivotally connected to the rocker arms 310 which are pivotally mounted on boss portions 312 (FIG. 2) extending inwardly from the side panels 104 and 106 of the upper supporting frame 22. The rocker arms 310 are provided with slots 314 which receive a guide pin 316 extending outwardly from the depending flange portions 318 of the sleeves 176. Accordingly, as the table 20 is lowered from the tilted position shown in FIG. 9 to the horizontal position shown in FIG. 8 the footstep draw bars 40 are moved from the acute angle shown in FIG. 9 to the substantially horizontal positions shown in FIG. 8. The switch 306, which controls the solenoid valve 302 is adjustably positioned on the side wall 106 and is arranged to be opened by engagement by the footstep draw bar 40 adjacent the panel 106 when this draw bar approaches the horizontal position shown in FIG. 8.

The solenoid valve 302 is open during periods when AC power is supplied thereto. However, when the switch 306 is opened the solenoid valve 302 is closed so that the hydraulic cylinder 220 may now be exhausted only through the restriction port 304. The size of the restriction port 304 may be adjusted by means of the thumb screw 320 to get a desired slow rate of travel of the table 20 during the cushioning period. During this time the check valve 322 prevents bypassing of the restriction port 304. If the doctor desires to vary the duration of the cushioning period he can simply adjust the position of the switch 306 on the panel 106 which will vary the point at which this switch is opened and the solenoid valve 302 closed.

When it is desired to tilt the table 20 upwardly, the foot switch arm 270 is depressed by the doctor so as to supply oil under pressure to the line 300. During the first few degrees of tilt of the table 20 the solenoid valve 302 remains closed since the switch 306 is still being actuated by the footstep draw bar 40. However, the application of pressure to the line 300 opens the check valve 321 so that the port 304 is bypassed and full hydraulic pressure is applied to the rod side of the piston 240 so that the table is elevated at maximum speed. As soon as the table is tilted an amount such that the switch 306 is closed, the solenoid valve 302 is again opened. In this connection it will be understood that the check valve 321 may be eliminated and the restriction port 304 will then remain in effect for both tilting the table 20 upwardly and downwardly near the horizontal position if the slow action in tilting the table upwardly does not introduce an undesired delay.

The switch 266 is employed to control the maximum tilt of the table 20 by engagement with the edge of the rocker arm 310, as shown in FIG. 9, when the table reaches a desired maximum tilt position. When the table 20 reaches the position shown in FIG. 9 the switch 266 is opened and the solenoid valves 256, 258 are deenergized even though the doctor continues to depress the foot switch arm 270.

In accordance with a further aspect of the invention, the upper frame 22 is provided with downwardly extending side walls 322, 324 (FIG. 5) which together with the nosepiece 202 substantially completely enclose the rocker arm linkages when the table is in the minimum height position shown in FIG. 8. Also, the base 24 is provided with upstanding side walls 326, 328 and front wall 330 which further shield the linkages as the table 20 is being elevated so as to minimize the exposure of these linkages and consequent danger to the patient or the doctor. If desired, the curtains 332, 334 may be slidably mounted on the inner sides of the side walls 322, 324 and extend downwardly over the side walls 326, 328 of the base 24, as shown in the embodiment of FIG. 15. The curtains 332, 334 may, for example, have mounting slots 336 for slidably mounting the curtains on pins 338 extending inwardly from the sidewalls 322, 324. Such an arrangement provides total enclosure of the rocker arm linkages so that no pinch points are accessible to the doctor or the patient.

What is claimed as new and desired to be secured by Letters Patent of the United States is:

1. A patient treatment table, comprising a support frame, an upper frame, a patient table pivotally mounted on said upper frame and having an offset arm portion, a cylinder and piston assembly having relatively movable portions one of which is the piston portion of said assembly and the other of which is the cylinder portion of said assembly, means connecting one of said movable portions of said assembly to said offset arm portion, means for introducing fluid under pressure into one end of said cylinder to lower said patient table from a tilted position near the vertical into engagement with said upper frame, said engagement of said patient table with said upper frame preventing further movement of said one movable portion upon the continued application of fluid under pressure to said one end of said cylinder, and means responsive to movement of the other movable portion of said assembly upon the continued application of fluid under pressure to said one end of said cylinder after engagement of said patient table with said upper frame for elevating both said patient table and said upper frame relative to said support frame.

2. The patient treatment table of claim 1, which includes means for selectively adjusting the height to which said patient table and said upper frame are elevated relative to said support frame.

3. The patient treatment table of claim 2, wherein said height adjusting means includes switch means, means responsive to movement of said other movable portion of said assembly to a predetermined location for actuating said switch means, and means responsive to said actuation of said switch means for terminating the introduction of fluid under pressure to said one end of said cylinder.

4. The patient treatment table of claim 1, which includes means operative after said upper frame and patient table have been elevated to a desired height for preventing the flow of fluid out of said cylinder, thereby to support said patient table and upper frame at said desired elevated position.

5. A patient treatment table, comprising a support frame, an upper frame, a patient table pivotally mounted on said upper frame and having an offset arm portion, a control cylinder having a head end and a piston rod extending from the other end thereof, means connecting said piston rod to said offset arm portion, means for introducing fluid under pressure into said head end of said cylinder to lower said patient table from a tilted position near the vertical into engagement with said upper frame, a rocker arm assembly comprising a pair of rocker arms and a shaft interconnecting a point on said rocker arms intermediate the ends thereof, means for pivotally mounting said shaft on said upper frame with said shaft extending transversely thereof, a transversely extending member interconnecting one end of said rocker arms, means rotatably mounting the other ends of said rocker arms on said support frame, and means pivotally interconnecting said head end of said cylinder and said transversely extending member so that movement of said cylinder after said patient table is in engagement with said upper frame is effective to elevate said patient table and said upper frame relative to said support frame.

6. The patient treatment table of claim 5, wherein said rocker arm assembly is an integral casting.

7. The patient treatment table of claim 5, which includes a second pair of rocker arms, means pivotally mounting said second pair of rocker arms on said upper frame at the end thereof opposite said rocker arm assembly, means pivotally mounting one end of said second pair of rocker arms on said support frame, and means interconnecting the other ends of said second pair of rocker arms with said transversely extending member so that said second pair of rocker arms are moved in unison with said rocker arm assembly.

8. The patient treatment table of claim 5, wherein said pivotal interconnecting means includes a split bearing having a removable portion which is accessible from one end of said upper frame to facilitate removal of said cylinder.

9. A patient treatment table, comprising a support frame, an upper frame, a patient table pivotally mounted on said upper frame and having an offset arm portion, a control cylinder having a head end and a piston rod extending from the other end thereof, means connecting said piston rod to said offset arm portion, means for introducing fluid under pressure into said head end of said cylinder to lower said patient table from a tilted position into engagement with said upper frame, a plurality of rocker arms pivotally mounted on said upper frame at each end thereof, means for rotatably connecting one end of said rocker arms to said support frame, means interconnecting the other end of said rocker arms with said head end of said control cylinder so that said rocker arms are rotated about the pivotal mounting thereof in response to movement of said cylinder after said patient table is in engagement with said upper frame, thereby to elevate said patient table and said upper frame relative to said support frame.

10. The patient treatment table of claim 9, which includes means for controlling the height to which said patient table and said upper frame are elevated.

11. The patient treatment table of claim 10, wherein said height adjusting means includes switch means, means responsive to movement of said cylinder to a predetermined location for actuating said switch means, and means responsive to said actuation of said switch means for terminating the introduction of fluid under pressure to said head end of said cylinder.

12. The patient treatment table of claim 11, wherein said switch means is carried by said upper frame and is positioned to be actuated in response to movement of one of said rocker arms to a predetermined location.

13. The patient treatment table of claim 12, which includes a control lever pivotally mounted on said upper frame and having said switch means mounted thereon, and means for adjustably locking said control lever in different positions, thereby to vary the height to which said patient table and upper frame are elevated.

14. The patient treatment table of claim 9, which includes means operable independently of the engagement of said patient table with said upper frame for limiting movement of said piston relative to said upper frame after said patient table has been moved into engagement with said upper frame.

15. The patient treatment table of claim 10, wherein said rocker arms are pivotally mounted on said upper frame at points intermediate the ends of said rocker arms, the length of said rocker arms between said one ends and said intermediate points being approximately three times the lengths of said rocker arms between said intermediate points and said other ends of said rocker arms.

16. A patient treatment table, comprising a support frame, an upper frame, a patient table pivotally mounted on said upper frame at one end thereof and having a pair of spaced apart offset arm portions, a transverse rod interconnecting the ends of said arm portions, a control cylinder having a head end and a piston rod extending from the other end thereof, means pivotally connecting said piston rod to said transverse rod, means for introducing fluid under pressure into said head end of said cylinder to lower said patient table from a tilted position into a horizontal position in engagement with said upper frame, positive stop means carried by said upper frame and engaging said transverse rod for limiting further movement of said piston rod relative to said upper frame when said patient table is moved into engagement with said upper frame, and means responsive to movement of said cylinder after movement of said piston rod is limited by said positive stop means for elevating said patient table and said upper frame relative to said support frame.

17. A patient treatment table, comprising a support frame, an upper frame mounted on said support frame, a patient table having a foot end pivotally connected to said upper frame and including an offset arm portion, a single control cylinder having a piston rod pivotally connected to said offset arm portion, means responsive to the application of fluid under pressure to one side of said cylinder for lowering said patient table from a tilted position near the vertical to a horizontal position in which said patient table engages said upper frame, said piston rod being held in a fixed position relative to said upper frame when said patient table is in engagement with said upper frame, and means responsive to the continued application of fluid under pressure to said one side of said cylinder while said piston rod is held in said fixed position for immediately elevating both said patient table and said upper frame relative to said support frame.

18. A patient treatment table comprising an upper housing, a patient table pivotally connected to said upper housing at one end thereof, a lower support frame, a plurality of rocker arms pivotally mounted on said upper housing at each end thereof, means for rotatably connecting one end of said rocker arms to said support frame so that said housing is supported in a lower horizontal position in which said housing substantially encloses said rocker arms and said support frame, a cylinder and piston assembly for raising said upper housing to a desired level with respect to said support frame, said assembly having relatively movable portions one of which is the piston portion of said assembly and the other of which is the cylinder portion of said assembly, means interconnecting the other end of said rocker arms with one movable portion of said cylinder and piston assembly so that said other ends move in unison therewith, said patient table including an offset arm portion, and means connecting the other movable portion of said assembly to said offset arm portion so that movement of said other movable portion toward said one movable portion causes said patient table to tilt upwardly relative to said upper housing.

19. The patient treatment table of claim 18, which includes a cross member formed integrally with and interconnecting said other ends of a pair of said rocker arms, and means pivotally connecting said head end of said cylinder to said cross member.

20. A patient treatment table, comprising a support frame, an upper frame mounted on said support frame, a patient table having a foot end pivotally connected to said upper frame, a single control cylinder assembly having relatively movable portions one of which is the piston portion of said assembly and the other of which is the cylinder portion of said assembly, means connecting one of said movable portions of said assembly to said patient table, linkage means interconnecting said upper frame and said support frame, means connecting the other one of said movable portions of said assembly to said linkage means, and means responsive to the application of fluid under pressure to one side of said cylinder for first lowering said patient table from a tilted position near the vertical to a horizontal position by movement of said one movable portion while said other movable portion remains fixed relative to said upper frame and then immediately thereafter elevating both said patient table and said upper frame relative to said support frame by movement of said other movable portion of said assembly while said one movable portion remains fixed relative to said upper frame.

21. The patient treatment table of claim 20, which includes means responsive to engagement of the head end of said patient table with said upper frame for fixing said one movable portion relative to said upper frame, thereby to initiate elevation of said patient table and upper frame in response to movement of said other movable portion of said assembly upon the continued application of fluid under pressure to said one side of said cylinder.

22. The patient treatment table of claim 20, wherein said horizontal position is established by engagement of the head end of said patient table with said upper frame, and means on said upper frame and operative independently of said engagement of said patient table with said upper frame for limiting movement of said one movable portion relative to said upper frame during elevation of said patient table and upper frame.

23. A patient treatment table, comprising a support frame, an upper frame, a patient table pivotally mounted on said upper frame and having an offset arm portion, a control cylinder having a head end and a piston rod extending from the other end thereof, means connecting said piston rod to said offset arm portion, a plurality of rocker arms pivotally mounted on said upper frame at each end thereof, means for rotatably connecting one end of said rocker arms to said support frame, means interconnecting the other end of said rocker arms with said head end of said control cylinder, means for introducing fluid under pressure into said head end of said cylinder while said patient table is in engagement with said upper frame so that said patient table and said upper frame are elevated relative to said support frame, and means for introducing fluid under pressure to the piston rod end of said cylinder, thereby to tilt said patient table about the pivotal mounting thereof to a position near the vertical.

24. The patient table of claim 23, wherein said piston rod is fixed relative to said upper frame when said patient table and said upper frame are elevated relative to said support frame, and said cylinder is fixed relative to said upper frame when said patient table is tilted to said position near the vertical.

* * * * *

UNITED STATES PATENT AND TRADEMARK OFFICE
CERTIFICATE OF CORRECTION

PATENT NO. : 4,401,110

DATED : August 30, 1983

INVENTOR(S) : Carl R. Ekholm

It is certified that error appears in the above-identified patent and that said Letters Patent are hereby corrected as shown below:

Column 13, line 55, "10" should read --9--.

Signed and Sealed this

*Eighth* Day of *November 1983*

[SEAL]

*Attest:*

GERALD J. MOSSINGHOFF

*Attesting Officer* — *Commissioner of Patents and Trademarks*